United States Patent [19]

Law et al.

[11] Patent Number: 5,762,066
[45] Date of Patent: Jun. 9, 1998

[54] MULTIFACETED ULTRASOUND TRANSDUCER PROBE SYSTEM AND METHODS FOR ITS USE

[75] Inventors: Wing K. Law, Mountain View; Carl Hennige, San Jose, both of Calif.; Frank Fry, Port Charlotte, Fla.; Narendra T. Sanghvi, Indianapolis, Ind.; Fred Miller, Fremont, Calif.; Paul Kendrick, Sunnyvale, Calif.; Stan DeMarta, Pleasanton, Calif.

[73] Assignee: THS International, Inc., Indianapolis, Ind.

[21] Appl. No.: 446,503

[22] Filed: May 22, 1995

Related U.S. Application Data

[63] Continuation-in-part of Ser. No. 840,502, Feb. 21, 1992, abandoned.
[51] Int. Cl.⁶ .................................. A61B 17/22; A61B 8/12
[52] U.S. Cl. .............................. 128/660.03; 128/662.06; 601/3
[58] Field of Search ................ 128/660.03, 662.06; 601/3

[56] References Cited

U.S. PATENT DOCUMENTS

| | | | |
|---|---|---|---|
| 4,237,901 | 12/1980 | Taenzer | 73/644 X |
| 4,748,985 | 6/1988 | Nagasaki | 128/4 X |
| 4,784,148 | 11/1988 | Dow et al. | 128/662.01 |
| 4,850,363 | 7/1989 | Yanagawa | 128/662.06 X |
| 4,913,155 | 4/1990 | Dow et al. | 128/660.1 |
| 5,036,855 | 8/1991 | Fry et al. | 128/660.03 |
| 5,391,197 | 2/1995 | Burdette et al. | 601/3 |
| 5,402,792 | 4/1995 | Kimura | 128/663.01 |
| 5,471,988 | 12/1995 | Fujio et al. | 128/660.03 |
| 5,492,126 | 2/1996 | Hennige et al. | 128/662.06 X |
| 5,513,639 | 5/1996 | Satomi et al. | 128/662.06 X |

*Primary Examiner*—Francis Jaworski
*Attorney, Agent, or Firm*—Barnes & Thornburg

[57] ABSTRACT

A High Intensity Focused Ultrasound system is provided for treatment of focal disease. The preferred embodiment includes an intracavity probe having two active ultrasound radiating surfaces with different focal geometries. Selectively energizing the first surface focuses therapeutic energy a first distance from the housing, energizing the second surface focuses therapeutic energy nearer the housing. Preferably, the probe includes a thin, flexible, inelastic membrane which is rigidized with pressure to allow blunt manipulation of tissue. Methods of use of the probe are also provided, particularly for treatment of diseases of the prostate.

9 Claims, 6 Drawing Sheets

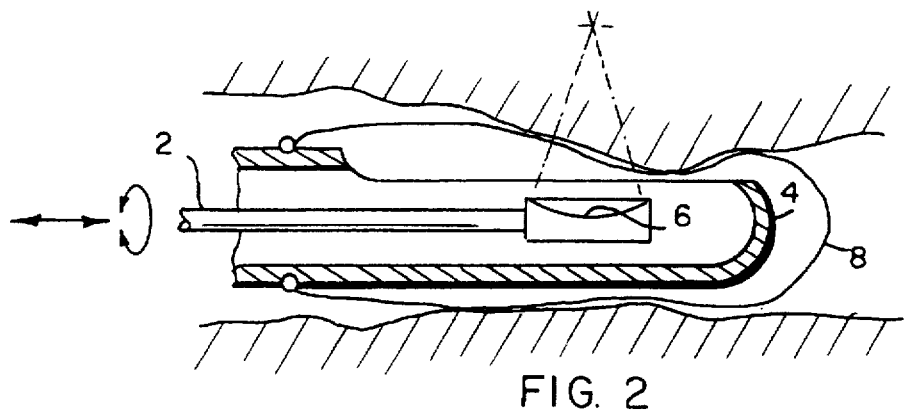
FIG. 2
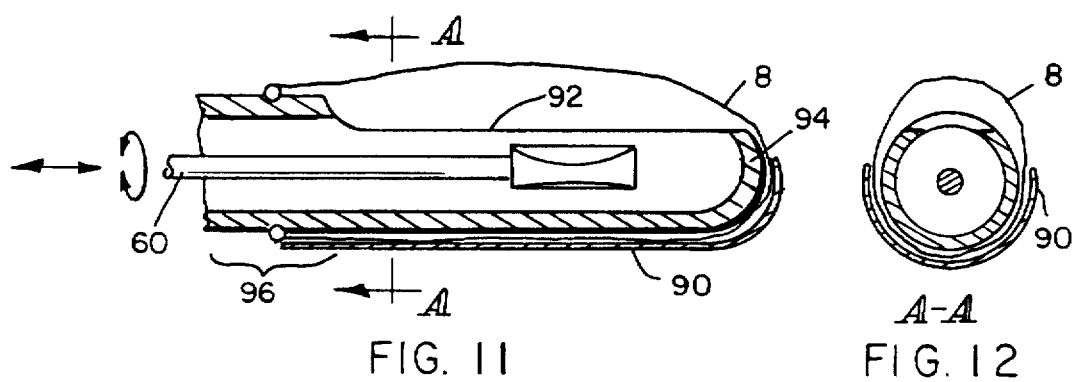
FIG. 11                    FIG. 12
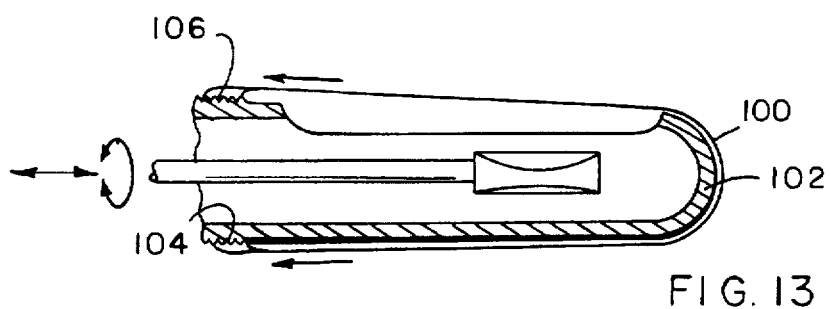
FIG. 13
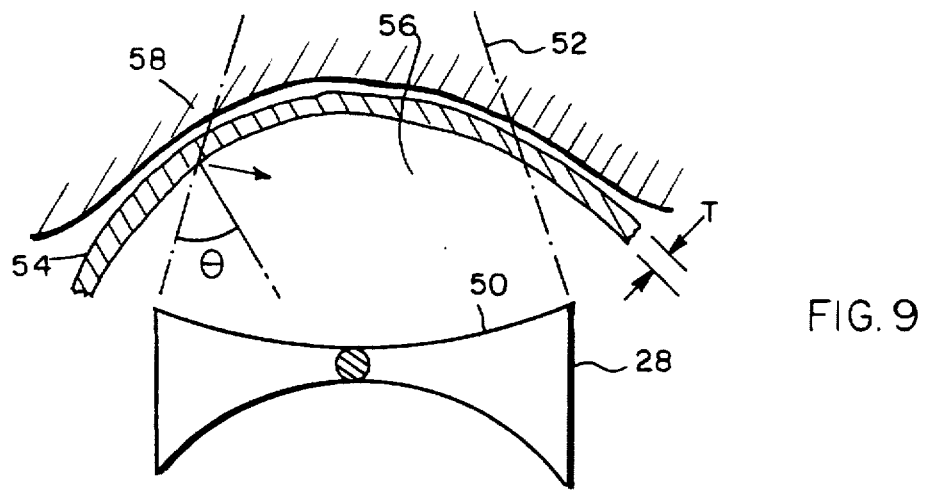
FIG. 9

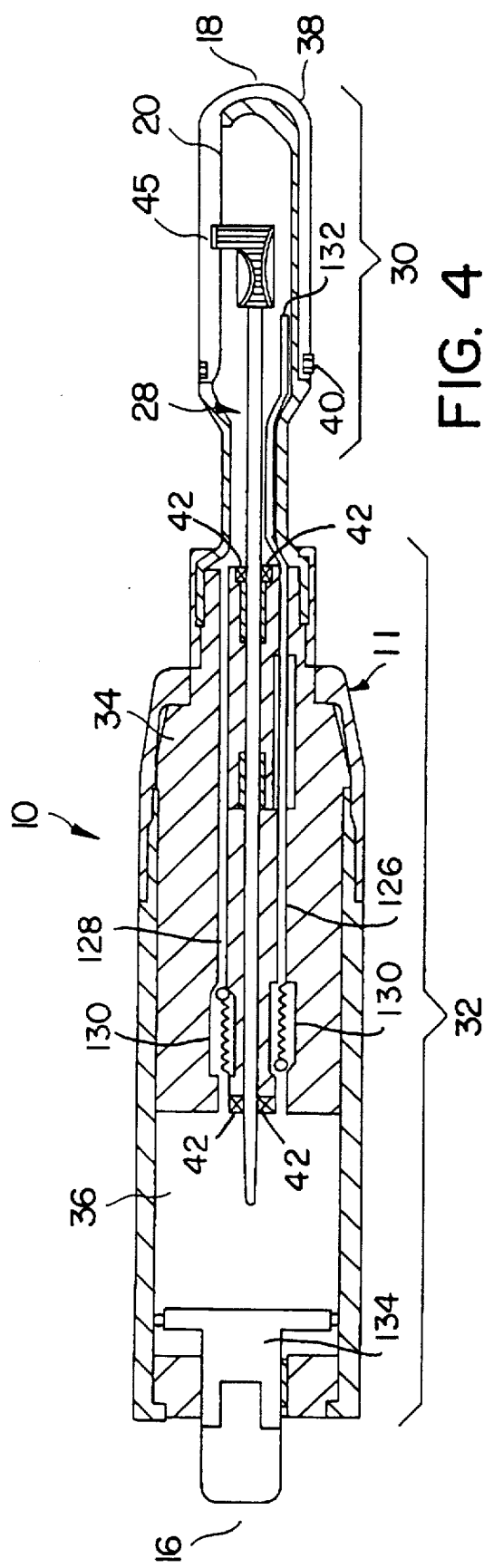
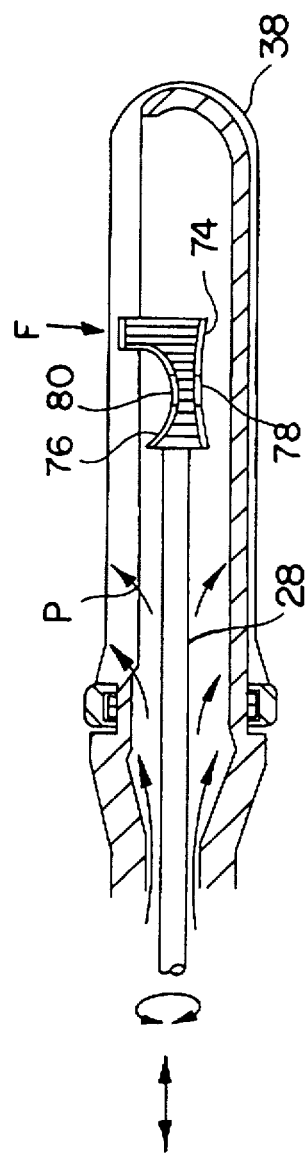

MULTIFACETED ULTRASOUND TRANSDUCER PROBE SYSTEM AND METHODS FOR ITS USE

This application is a Continuation-in-Part of application Ser. No. 07/840,502, filed Feb. 21, 1992, now abandoned the full disclosure of which is incorporated herein by reference.

BACKGROUND OF THE INVENTION

1. Field of the Invention

The present invention relates generally to the localization and therapy of localized diseases. In particular, the present invention provides a High Intensity Focused Ultrasound system having a multifaceted transducer, together with methods of using such a system for guidance and application of therapeutic ultrasound energy at varying focal distances.

The use of ultrasound for imaging and diagnosis of disease is well known in the medical field. Ultrasound imaging generally relies on differences in the reflection of high frequency acoustic waves by solid structures, such as bones, and by soft tissues. Ultrasound waves, when applied at power levels required for imaging, have not been found to have the deleterious side effects associated with many other forms of radiated energy, such as X-rays, microwaves, and other electromagnetic fields. Hence, ultrasound imaging systems have a distinct advantage over other known imaging modalities.

Generally, ultrasound waves are radiated from and the reflections sensed by a transducer. Imaging ultrasound transducers are known to make use of multiple radiating and/or receiving active surfaces. For example, modern ultrasound probes often use precise timing control over a series of active surfaces, referred to as a phased array, to control the radiation direction and to sense the source of reflections. Ultrasound imaging systems having multiple transducer surfaces have also been proposed for imaging objects at different distances from the probe. For example, one proposal is to use a scanning ultrasound transducer having a plurality of radially oriented active surfaces with differing focal lengths to synthesize an image covering a wider reflection range.

Multifaceted ultrasound imaging transducers are now in use within extracorporal and, more recently, internal probes. Miniaturization of internal ultrasonic imaging transducers and probes has now progressed to the point that intravascular ultrasound (IVUS) is now well established. This miniaturization has been made possible,in part, by low imaging power requirements.

Although ultrasound imaging waves are noted for its safety, ultrasound energy applied at higher power densities can have significant physiological effects on tissues. These physiological effects may result from either thermal or mechanical effects of ultrasound on tissues. Thermal effects of ultrasound heating include hyperthermia and ablation of tissue (with relatively low energy levels), and even rapid high temperature searing. Mechanical effects include breaking-up of solid objects, liquefaction of tissues, and cavitation.

These effects of high power ultrasound can occur adjacent the ultrasound radiating surface, or they may be produced at a distance from the radiating surface by focusing of the ultrasonic waves at a target region within the tissue. For example, lithotriptors use a large external radiating surface to focus short bursts of ultrasound energy as shock waves inside a patient body, thereby mechanically fragmenting kidney stones. Clearly, the ultrasound must be focused on a target region which is very small relative to the transmitting surface to avoid affecting the intermediate tissue. Therefore, the therapeutic ultrasound radiating surfaces have remained quite large, utilizing extracorporal devices and equipment.

The large size and power of therapeutic ultrasound devices has prevented the transfer of imaging ultrasound transducer technology to ultrasound therapy. Most proposed ultrasound therapy devices have relied on positioning of the patient body relative to a single large spherical radiating surface, with the body and surface being acoustically coupled by a water bath, fluid filled bag, or the like. This theoretically allows treatment to be targeted at any point in the body, but suffers from significant inaccuracy as the waves pass through differing tissues, and as targeted tissues move within the body. Although similar drawbacks in ultrasound imaging have been overcome by multifaceted intracorporal imaging probes, the size requirements for each focusing ultrasound radiating surface has generally discouraged practical proposals against introduction of multiple therapeutic ultrasound radiating surfaces into a patient body.

Nonetheless, the use of High Intensity Focused Ultrasound (herein referred to as "HIFU") has been proposed as a therapy for diseases which manifest themselves in a localized or "focal" manner. Focal diseases for which HIFU has been suggested include, for example, neoplastic and other diseases of or in the brain, breast, liver, and prostate. Although surgical procedures have been developed for these diseases, and are routinely employed when medicinal approaches are not suitable or effective, such surgery often represents a significant risk to the patient. Moreover, efficacy of the surgery is often limited by a possibility that not all of a diseased tissue has been removed, requiring additional surgery with its added risk. In contrast, HIFU therapy potentially offers a non-invasive or minimally invasive alternative, in which each treatment inflicts much less trauma on the patient, providing a more easily controlled procedure, and promoting faster healing.

Specifically addressing a common focal disease of the prostate, HIFU therapy has recently been applied as a treatment for Benign Prostatic Hyperplasia (herein referred to as BPH). BPH is a widespread disease in males generally involving gradual enlargement of the prostate gland. As the prostate enlarges, it commonly leads to obstruction of the urethra in the region below the bladder.

A variety of techniques have previously been developed for treatment of BPH. For example, balloon dilation has been used to enlarge the urethra in the obstructed region. However, symptoms of obstructive voiding often recur within one to two years of the dilation procedure. Another well known procedure for BPH treatment is transurethral resection (herein referred to as TUR). TUR involves positioning a resectoscope through the urethra into the prostate, and using a cutting instrument, such as a heated wire, to incise obstructing portions of the prostate. Unfortunately, TUR commonly produces a number of undesirable side effects, including retrograde ejaculation, urinary retention, and impotence. Moreover, TUR procedures have a morbidity rate as high as 25%.

Other alternative techniques have recently been suggested for the treatment of BPH. For example, both microwave prostatic ablation and direct laser ablation of the prostate have been proposed. Although a transrectal microwave antenna may potentially be effective, there are concerns about secondary effects on the rectal wall and the other intermediate, healthy tissues. Laser therapies generally involve physical penetration of the urethra and prostatic tissue for delivery of the ablation energy by one or more inserted optical fibers, and therefore introduce risk of infection.

Parent U.S. application Ser. No. 07/840,502, the full disclosure of which is herein incorporated by reference, describes a HIFU system and method which has proven effective for the treatment of BPH. This exemplary HIFU system includes a probe housing which contains a focusing therapeutic ultrasound transducer, and control means for controlling the transducer within the probe.

The probe disclosed in application Ser. No. 07/840,502 contains a transducer capable of applying and focusing therapeutic ultrasound energy at a target region which lies at a fixed focal distance from the transducer surface. The transducer has a single crystal active surface which conforms to a body of revolution, such as a sphere or an ellipsoid. Two edges are included in the transducer to reduce the overall transducer and probe width, facilitating transrectal insertion, while maintaining sufficient active surface area for ultrasonic therapy. Finally, a limited region of the transducer surface is capable of independent ultrasound imaging. The exemplary transducer is more fully described in U.S. Pat. No. 5,117,832, the full disclosure of which is also herein incorporated by reference.

The disclosed probe further includes mechanical means for sector and linear scanning of the patient, by moving a transducer shaft in cylindrical coordinates within a probe housing. The positioning means are used both for image scanning in localization of the focal disease, and for aiming of the focal region in application of therapeutic ultrasound energy. The housing includes an open window to allow passage of the ultrasonic energy to the patient. To couple the transducer surface to the rectal wall, the distal end of the probe surrounding the transducer is filled with water. A flexible elastic membrane sheath covers a distal end of the probe housing, extending over the open window, to retain the coupling water. The membrane is conveniently in the form of a common latex condom. Water is supplied to the inner surface of the membrane through the probe housing.

Although the above described HIFU system and probe have proven highly effective as a tool for applying HIFU therapy for the treatment of BPH, it has been discovered by the inventors herein that the probe suffers from certain limitations which prevent the full realization of the potential benefits of HIFU therapy for the treatment of BPH, prostatic cancer, and for other focal diseases in general. First, the fixed focal length of the transducer limits the range and flexibility of the system from applying therapeutic energy to focal diseases which extend beyond a single fixed focal region located at a set distance from the probe housing. Second, although the elastic membrane provides efficient transmission of ultrasound energy, any tissue protruding into the rectal cavity poses a potential danger of entering the probe housing window and interfering with the scanning and positioning motion of the transducer. Finally, it is difficult to directly manipulate tissue using the elastic membrane of the existing probe, as movement of the probe relative to the patient may result in resilient flexing of the membrane rather than, for example, compression of a desired tissue.

The potential benefits of intracavity HIFU therapy are further limited by several additional factors. Clearly, the size of such a probe must be reduced to allow insertion, which limits the volume available for the active radiating surface area of the transducer. Furthermore, it has been discovered in connection with the present invention that power throughput with a small active surface is limited, in part, by the temperature rise in the entrapped coupling fluid. Additionally, ultrasound image quality is limited where an imaging transducer surface is disposed at a significant distance from the membrane/tissue coupling interface. Finally, the maximum focal range of a small, therapeutic ultrasound probe is limited by the active surface area of the transducer.

Moreover, the HIFU therapy systems and methods proposed to date, internal and extracorporal, suffer from certain common drawbacks. First, the relative positioning of the transducer surface in relation to the target tissue has been pliant, relying on fluid couplings and the like which are susceptible to movement during treatment. Second, HIFU hyperthermia treatment has been difficult to monitor. Thermal lesions are not clearly visible under ultrasonic imaging, making therapy target control problematic. Third, HIFU treatments have generally relied only on the thermal and mechanical effects of ultrasound energy on fixed tissues and structures. The potential application of therapeutic ultrasound energy on body fluids particularly for the coagulation of blood to control internal bleeding, has not previously been explored.

For these reasons, it would be desirable to provide therapeutic HIFU systems and methods which overcome the drawbacks and limitations of existing and currently proposed systems. It would be particularly desirable if a HIFU probe would permit selection of a particular focal length to enable treatment of target locations in tissue located at varying distances from the probe. The probe should eliminate the danger of protruding tissue interfering with the mechanical scanning of the transducer, and should further allow direct manipulation of tissue with the probe, but should not compromise the efficiency of the coupling between the active surface and the tissue. Furthermore, it would be desirable if a probe system could be developed which would increase throughput without increasing probe size or temperature. Finally, it would be particularly desirable if HIFU systems and methods were provided which maintain the therapeutic advantages of previous approaches, without the susceptibility to relative motion and without affecting surrounding tissue.

2. Description of the Background Art

U.S. Pat. No. 4,850,363 describes an ultrasonic diagnostic apparatus having multiple focal lengths. The apparatus synthesizes the reflected signals from a plurality of axially mounted rotating transducers into a single composite image. German Patent DE 3714-747-A also shows a pair of transducers rotatably mounted within an ultrasonic probe. U.S. Pat. No. 4,972,839 discloses a miniaturized ultrasonic imaging probe having back to back transducers which radiate at different frequencies.

Parent application Ser. No. 07/840,502, previously incorporated by reference, teaches an ultrasonic therapy and imaging probe system using sector and linear scanning with a single focal length transducer, as described above. U.S. Pat. No. 5,117,832, previously incorporated by reference, teaches an exemplary ultrasonic therapy and imaging transducer.

International Patent Application WO 93/17646 discloses a transrectal probe having a single focal length transducer. Published French Patent Application No. 91 02620 also discloses a transrectal ultrasound therapy probe. U.S. patent application Ser. No. 4,960,107 discloses an extracorporal ultrasound medical treatment apparatus having a transmitting surface formed of a plurality of piezoelectric elements of different shapes.

U.S. Pat. Reissue No. 33,590 is directed toward a method for examining, localizing, and treating with ultrasound. U.S. Pat. No. 5,143,074 discloses an ultrasonic treatment method in which the treatment transducer oscillates during therapy.

U.S. Pat. Nos. 5,320,106, 5,090,414, 4,390,414, and 4,674,515 each disclose intracavity ultrasonic imaging probes. Japanese Patent 5-184573 discloses an ultrasonic endoscope. U.S. Pat. No. 5,271,402 is generally relevant.

SUMMARY OF THE INVENTION

The present invention provides an improved High Intensity Focused Ultrasound (HIFU) system and methods for its use. In particular, the present invention provides an intracavity HIFU probe which allows the controlled application of therapeutic ultrasound energy to target locations in tissue which are disposed at varying distances from the probe. The probe of the present invention includes a probe housing containing a transducer having a plurality of active surfaces of differing focal lengths. By manipulation of the present transducer and applying energy to a selected active surface, the present HIFU system allows selective targeting of diseased tissues at varying distances from the probe housing. Thus the present invention allows improved precision over existing HIFU therapy systems.

In another aspect, the intracavity probe of the present invention also provides a therapeutic ultrasound probe having a rigidized acoustic membrane which provides efficient transmission of ultrasound energy, but which also allows direct engagement of the membrane to manipulate tissue, thereby aiding in positioning of the probe relative to the target. The rigidized acoustic membrane also allows movement of the transducer member within a probe housing without interference from protruding tissue, and thus eliminates a source of possible injury to such protruding tissues.

The present system will find applications in localization and treatment of a wide range of focal diseases, including cancers of the breast, brain, liver, and kidney. The intracavity probe of the present system will be particularly useful for focal diseases which are accessible to a transesophageal, laparoscopic or transvaginal probe. Such diseases include esophageal cancer, cancer in the trachea and urethra, ulcers in the stomach and duodenum, and pancreatic cancer. Moreover, a transvaginal probe according to the present invention will provide a minimally invasive sterilization procedure on an outpatient basis, as well as therapy for fibroids, and endometrial ablation. Additionally, the multiple focal lengths of the present probe will allow selective targeting of blood vessels and internal bleeding to effect coagulation and cauterization. The probes of the present system will have its greatest application as a transrectal probe in the localization and treatment of diseases of the prostate, including Benign Prostatic Hyperplasia (BPH) and prostatic cancer.

In a particularly preferred aspect, the present invention provides a transducer member having two radially opposed active surfaces of different focal lengths disposed within an intracavity housing having a rigidized acoustic membrane. optionally, each active surface is separated into an inner and outer region which allows electronic adjustment of the focal length as a simple phased array. In connection with the present invention, it has been discovered that such an intracavity probe having overlapping HIFU treatment ranges, and which also allows direct manipulation of the rectal wall against a rigidized membrane, generally provides a sufficient treatment range to selectively target all of the required tissues for effective treatment of prostatic focal disease.

To achieve such benefits and advantages, the present invention provides an ultrasound therapy probe comprising a housing and a plurality of active surfaces disposed within the housing. At least some of the active surfaces have different focal lengths, so that the probe is capable of focussing therapeutic ultrasound energy on at least two different target volumes at different distances from the housing. Usually, the transducer member is rotatably mounted within the probe housing, and the active surfaces are radially disposed about the transducer member, allowing rotation of the transducer member to provide selection and angular aiming of the plurality of active surfaces. Optionally, the probe housing includes an inelastic and non-distensible acoustic membrane to ensure that tissue does not protrude into an interior volume of the probe housing. In a preferred embodiment, a coupling fluid rigidizes the membrane, and preferably recirculates to cool the probe. Ideally, a degassed coupling fluid is used to prevent the formation of bubbles.

A preferred embodiment of the present ultrasound therapy probe comprises a housing which is adapted to be at least partially inserted into a patient body. The housing contains first and second active surfaces which are each capable of focussing therapeutic ultrasound energy, but which focus on target volumes at different distances from the housing. The effective range of therapy will vary with the size of the active surfaces, or more precisely, with the aperture size. Preferably, the target volumes overlap to provide a continuous therapy range, ideally extending at least from ½ the aperture to ⅔ the aperture size from the housing.

The present invention further provides a probe including a housing having a flexible, inelastic, and non-distensible acoustic membrane. Ultrasound energy is radiated from an active surface, and is coupled to the membrane by coupling fluid. The acoustic membrane transmits the ultrasound energy to an adjacent tissue, and advantageously will prevent the tissue from protruding into the housing. Preferably, the thickness of the present membrane is on the order of one ultrasonic wavelength or less. Ideally, the membrane thickness is one tenth of a wavelength or less. The membrane is thin, and therefore flexible in its relaxed state. The membrane has an impedance similar to tissue to allow efficient transmission of ultrasound energy, and is inelastic and non-distensible, to prevent the membrane from deforming significantly once it is held under tension. Preferably, the membrane is rigidized by maintaining a pressure of at least 0.5 psi, ideally being under a pressure of at least 1 psi. Suitable materials for the membrane of the present invention include PET, polyethylene, or the like.

Advantageously, the present thin, flexible membrane provides a more efficient transmission of ultrasonic energy, specifically reducing critical angle phenomenon losses, as compared to membranes of known imaging probes, which typically rely on the strength of a thick membrane for support. Furthermore, a transducer disposed behind such a thin, rigidized membrane is free to rotate, without fear of injury to tissues protruding into the probe housing. This avoiding of protruding tissue is of particular importance when the probe housing contains a multifaceted transducer which must be rotated to select an active surface.

Certain embodiments of the present probe housing utilize means for placing the membrane under tension to stress the membrane. One tension-applying means comprises a cylindrical membrane disposed about the probe housing, which housing extends distally to a sealed distal end of the membrane. The proximal end of the membrane is attached to the probe housing by a threaded fitting. Thus, by rotating the membrane relative to the housing, the cylindrical membrane is axially translated relative to the housing and "stretched" in order to provide tension. The membrane will be stressed sufficiently so that a force against the outer cylindrical membrane surface, for example by a radial movement of the probe which compresses tissue against the membrane, will not significantly distort the cylindrical shape of the membrane.

In a preferred alternative embodiment, the tension-applying means of the probe includes a pressurized coupling fluid acting on one side of membrane. A particularly advantageous acoustic membrane for use with a pressurized coupling fluid comprises a cylindrical membrane disposed about the transducer, which membrane is sealed at the distal end. A proximal end of the membrane is sealingly attached to the probe housing. Contained within the membrane interior volume is a fluid at a pressure in the range from 1 psi to 100 psi, preferably being in the range from 1 psi to 5 psi.

The present invention further provides an improved ultrasonic probe having a fluid pressurization system. A probe having a fixed interior volume and an axially movable transducer member disposed, in part, in the interior volume further includes a first lumen and a reservoir in fluid communication with the interior volume. Advantageously, changes in displacement caused by movement of the transducer member are compensated for by a flow of coupling fluid between the interior volume and the reservoir. Ideally, the pressurization system includes a recirculating fluid path, which circulates coupling fluid during displacement of the transducer member into and out of the interior volume. Advantageously, such a pressurization system not only provides rigidity to the membrane, but also acoustically couples an active surface of the transducer member to the membrane, and may also be used to cool and eliminate bubbles from the coupling fluid.

In connection with the present invention, it has been discovered that the much greater power levels associated with HIFU therapy causes an increase in cavitational effects on a coupling fluid. These effects result in the formation of bubbles which block ultrasound energy, and which distort and reflect the ultrasound waves. It: has further been discovered that a degassed liquid increases acoustic coupling efficiency and resolution for HIFU therapy, and to a lesser extent, for imaging ultrasound as well. Surprisingly, a degassed fluid has been found to absorb bubbles which are formed, thereby improving resolution and efficiency. Therefore, the present invention provides an improved ultrasound coupling fluid for acoustically coupling an active surface to a tissue, the coupling fluid comprising a degassed liquid. The degassed liquid is preferably degassed water, ideally having an entrapped oxygen content of less than 3 parts per million. Ideally, the present coupling fluid has a velocity which matches the velocity of the adjacent tissue to avoid any distortion of the focussed ultrasound energy through a curved coupling fluid/tissue interface.

The present invention also provides methods for the treatment of focal disease using HIFU. A first embodiment of the present method comprises acoustically coupling a probe to a body, and focussing therapeutic ultrasound energy from the probe on a first volume of tissue at a first distance from the probe. At least one active surface is energized to treat the first volume. The method further includes focussing energy on a second volume a second distance from the housing, by energizing at least one alternate active surface. Usually, a first and second active surface are energized having first and second focal lengths, respectively, which focal lengths are different. Preferably, the present method further comprises positioning the probe relative to a diseased tissue by compressing an intermediate tissue against a thin, flexible, inelastic, and non-distensible acoustic membrane.

An alternative embodiment of the present method comprises transrectally inserting a probe, focussing therapeutic ultrasound energy from the probe to a first volume of the prostate a first distance from the probe, and focussing therapeutic ultrasound energy on a second volume of the prostate at a second distance from the probe which is different from the first distance. Preferably, the present method further comprises compressing of a rectal tissue against a thin, flexible, inelastic and non-distensible acoustic membrane to position the probe relative to the prostate. Advantageously, such a method allows application of HIFU therapy throughout the range of prostatic tissue required for effective treatment of BPH, prostatic cancer, and other diseases of the prostate.

A further understanding of the nature and advantages of the present invention may be realized by reference to the attached drawings and descriptions of the specific embodiments.

BRIEF DESCRIPTION OF THE DRAWINGS

FIG. 2 is a cross-sectional view of a known therapeutic ultrasound probe shown positioned in a body cavity.

FIG. 4 is a cross-sectional view of one embodiment of the present therapeutic ultrasound probe.

FIG. 9 is a schematic end view of the present multifaceted transducer member behind a cylindrical rigid membrane to illustrate the critical angle phenomenon.

FIG. 10 is a cross-sectional view of a preferred multifaceted transducer within a preferred embodiment of the present probe having a thin, flexible, inelastic and non-distensible membrane rigidized by coupling fluid pressure.

FIGS. 11 and 12 are cross-sectional views of the present multifaceted transducer within one embodiment of the present intracavity probe.

FIG. 13 is an alternative embodiment of the thin flexible, inelastic membrane, wherein the membrane is rigidized by tension.

DESCRIPTION OF THE PREFERRED EMBODIMENT

Figure 1:
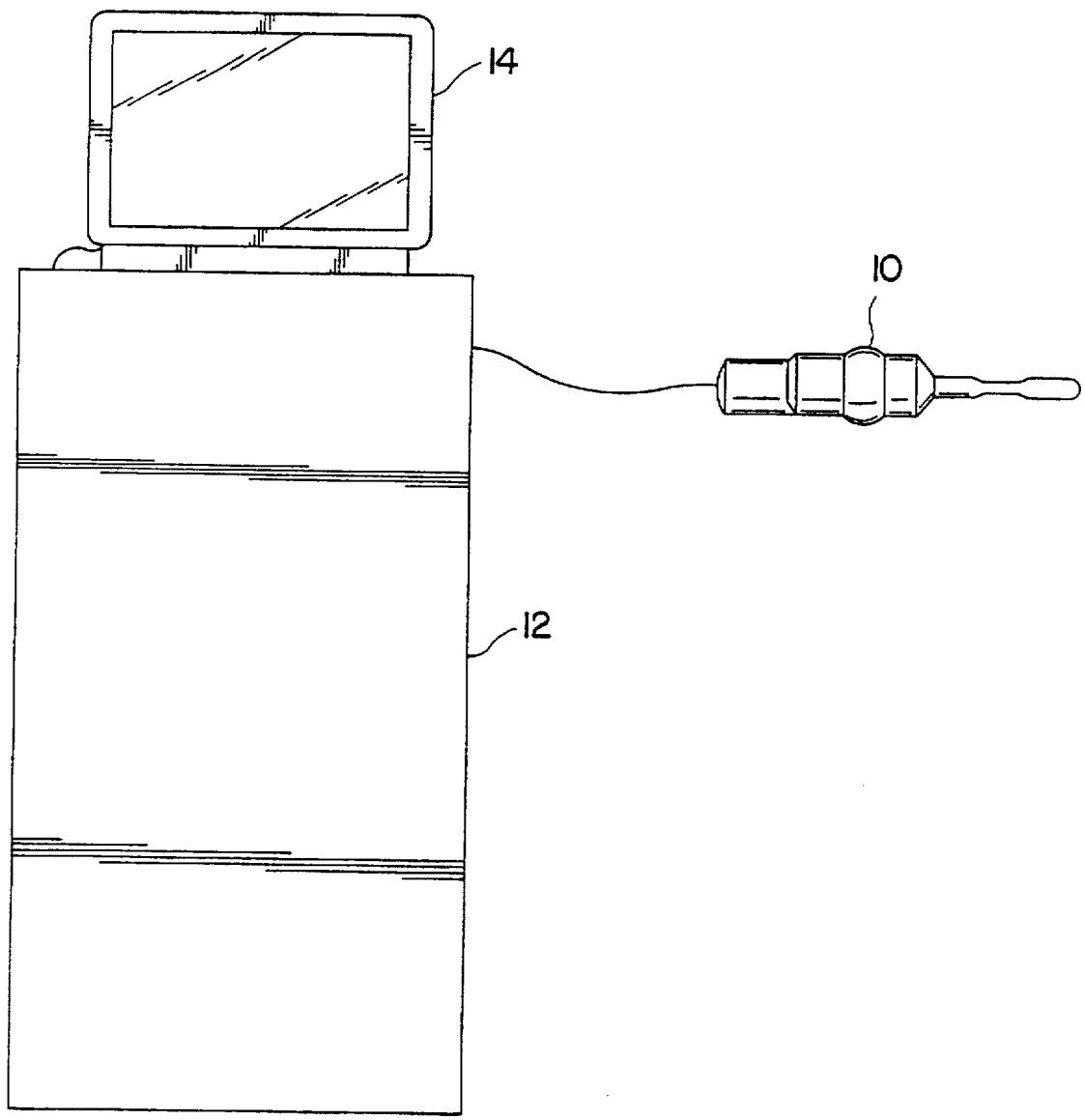
FIG. 1 is a schematic view of a HIFU system, including the therapeutic ultrasound probe and control means, according to the present invention.

The present invention provides a High Intensity Focused Ultrasound (HIFU) system for the treatment of focal disease. The HIFU system of the present invention will find a wide range of applications for the localization and treatment of diseases which are manifest in discrete areas or tissues, including neoplastic and other diseases of the brain, liver, breast, and prostate. The present invention will have particular applications to cancers of these and other tissues, which are now often treated by open surgical procedures to remove the cancerous tissues. HIFU treatment offers a non-invasive or minimally invasive alternative which allows application of ablative energy from outside the effected organ, by application and concentration of ultrasound energy specifically on the diseased tissue. Ultrasound energy offers a recognized safety advantage as compared to alternative electromagnetic energy transmission modalities. Thus, therapies which rely on focussing of ultrasound energies on diseased tissues minimize damage to the surrounding healthy tissues of the patient, and thereby greatly promote healing.

The present intracavity HIFU system allows extra corporal, laparoscopic, transrectal, transesophageal, transtracheal, transvaginal, or transurethral application of HIFU therapy. Although such systems will thus have applications to a wide range of focal diseases, the present intracavity HIFU therapy system will find its greatest application in the treatment of Benign Prostatic Hyperplasia (BPH), prostatic cancer, and other diseases of the prostate.

Specifically addressing the treatment of BPH, the HIFU intracavity system of the present application is capable of focusing therapeutic ultrasound energy at selected hyperplastic tissue of the prostate. In particular, the present invention provides a transrectal HIFU probe and control system which allows focusing of ultrasound energy through the rectal wall to target hyperplastic prostatic tissues which vary in distance from the probe housing. The present intracavity HIFU probe is further provided with a novel rigidized acoustic membrane which provides efficient acoustic coupling with the rectal wall, and which also allows compression and positioning of the targeted prostatic tissue relative to the probe housing by direct manipulation of the rectal wall against the acoustic membrane. Advantageously, the present probe is capable of selectively ablating hyperplastic prostatic tissue without the danger of morbidity associated with physical penetration of the urethra.

The methods of the present invention further provide increased effectiveness in the treatment of BPH by applying therapy while a catheter is present in the urethra. The catheter provides a contrast to assist imaging, and has been found to facilitate local heating. Steam formation and cavitation are increased adjacent to the catheter, further promoting the ablation of the targeted prostatic tissue. The catheter may conveniently be formed of silicon, latex, silicone coated latex, or PET.

The present invention also provides improved HIFU treatment methods which selectively apply therapy to a diseased region so as to allow blood perfusion cooling of the adjoining tissue. Alternating between separated treatment zones, or otherwise targeting individual focus volumes in an order which avoids sequential treatment of adjacent volumes, reduces the collateral heating of healthy, heat-sensitive tissues, particularly prostatic tissue.

The probe of the present invention will also find gynecologic applications. The present invention provides a transvaginal HIFU probe and method which provide a minimally invasive sterilization procedure that can be performed on an outpatient basis without general anesthesia or scaring. Preferably, thermal ablation of the horn and interstitial portion of the fallopian tube is performed after insertion of a contrast agent to facilitate target identification, ideally using color doppler imaging. Additional potential gynecological applications include endometrial ablation for treatment of menorrhagia, submucosal fibroid ablation, therapeutic abortion, and hyperthermic therapies for endometrial carcinoma, gestational trophoblastic disease, and the like.

The present probe will also have potential applications relying on the cavitational effects of HIFU. Movement of a focussed ultrasound beam which produces a cavitational bubble has been found to manipulate the bubble through tissue, effectively drilling and cutting internal tissues from a remote transducer HIFU cavitation has also been found to increase cell membrane permeability, allowing increased drug infusion and potentially providing a transport mechanism for gene therapy.

The present invention will have further applications in providing acoustic hemostasis. In connection with the present invention, HIFU has been found to coagulate blood and effect cautery of internal tissues and vessels. Thus, an extra corporal HIFU probe having color doppler imaging will find use in locating and controlling internal bleeding, and will be particularly advantageous for stabilizing of trauma victims. The current system is particularly suited for highly perfuse organs, such as the kidney, and will potentially inhibit inflammation of a portion of an organ before such inflammation spreads to the entire organ. Additionally, through coagulation, the present invention will find applications in reducing blood supplies to certain diseased sites.

The present HIFU methods and apparatus will have still further applications in drug activation. Drugs may be activated at specific treatment sites by the thermal or mechanical effects of ultrasound, minimizing side effects on healthy tissues. Activation may involve the release of caged drugs (for example, from liposome encapsulation), potentiation at elevated temperature, or increased permeation of the drug through cell membranes.

The term "transducer member" is used throughout this application to refer generally to an ultrasound radiator element having at least one active radiating surface. The transducer members of the present invention may further include a receiving surface for the sensing of acoustic reflections from tissues and objects.

This application, including the drawings, will occasionally refer to a "target point" of a focusing active surface. It should be understood that this is only done for simplicity and/or clarity of the drawings, as the actual effect of any focusing active surface will be to apply energy to a volume of tissue. Similarly, where the transducer member is moved in two directions, the spectrum of targets will at times be described as a surface or area. It should be understood that such targets will actually be cumulative target volumes. In fact, the target tissue will often have therapeutic energy applied as a series of individual, discrete focus target volumes, rather than as a continuously scanned region. Alternatively, a movement of the transducer during therapy will be beneficial in certain applications, particularly where a thin layer of lesion is desired.

System Overview

Referring now to FIG. 1, the ultrasound system of the present invention is schematically illustrated. The present ultrasound system includes a probe 10 and a controller 12. Controller 12 includes a display means 14, which is used to locate and select tissues for targeting of ultrasonic therapy.

An exemplary intracavity HIFU system, including a probe and a controller, are described in Parent application Ser. No. 07/840,502, previously incorporated by reference. As more fully described in that application, one intracavity HIFU treatment process comprises positioning a patient on a treatment table and transrectally inserting and positioning the treatment probe. A transducer disposed within the probe housing then images a tissue using a linear or sectoral scanning movement of the transducer relative to the housing. The operator next graphically selects a treatment volume as the target tissue, and also inputs treatment parameters. The controller automatically linearly and angularly positions the transducer so that the active surface is focused at the target tissue. The controller then activates the focused active surface of the transducer, applying therapeutic ultrasound energy to the target tissue.

The exemplary intracavity HIFU system described in Parent application Ser. No. 07/840,502 makes use of a transducer member with a fixed focal geometry, as illustrated in FIG. 2. In that system, a transducer member 2 is disposed within a generally cylindrical housing 4. Transducer member 2 has an active surface 6 which is capable of radiating focused therapeutic ultrasound energy at a fixed distance. Transducer member 2 is supported by positioning means which allow translation and rotation of the active surface within the housing, thereby allowing cylindrical aiming and scanning of the ultrasound energy. Transducer member 2 is coupled to adjoining tissue by coupling fluid and by an elastic acoustic membrane 8. Elastic membrane 8 is actually a standard latex condom.

The present intracavity probe and system provides significant additional capabilities through the use of an improved probe and a modified controller. The present probe includes a multifaceted transducer member, a rigidized acoustic membrane, and a membrane pressurization/recirculation system. Each of these elements will be discussed in detail hereinbelow.

The Probe and Probe Housing

Figure 3:
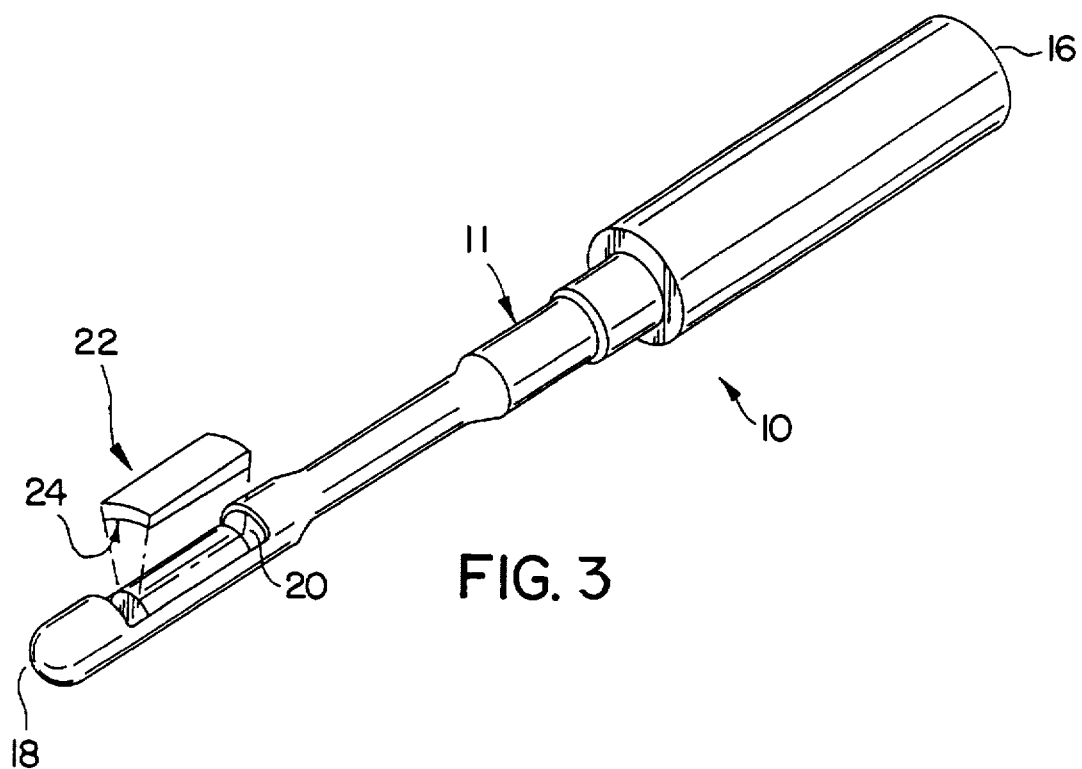
FIG. 3 is an orthogonal illustration of one embodiment of the present therapeutic ultrasound probe.

Referring now to the orthogonal probe overview illustration of FIG. 3, probe 10 includes a probe housing 11 having a proximal end 16, a distal end 18, and an acoustic window 20. The probe housing is shown without a membrane over window 20 for clarity. The distal portion of housing 10 contains a transducer member having back-to-back active surfaces with focal geometries at a first and a second distance from transducer member 28, respectively (see FIGS. 6 and 7). By rotating the transducer member within the housing and energizing these active surfaces independently, probe 10 is capable of applying HIFU therapy focused at a first distance 22 from housing 11, and also at a second distance 24 from housing 11. Generally, the actual first and second target volumes associated with these distances will at least be adjacent, and will preferably overlap, so that ultrasonic therapy can be applied to diseased tissues which lie throughout the volume between first distance 22 and second distance 24.

A cross-section of the present HIFU intracavity probe is shown in FIG. 4. Probe 10 includes probe housing 11 which contains a transducer member 28. Transducer member 28 features two back-to-back therapeutic ultrasound focusing active surfaces having different focal geometries. As described above, transducer member 28 can therefore target tissues at different distances. The transducer member will be described in detail hereinbelow. Probe housing 11 broadly includes a transducer region 30 near distal end 18, and a handle region 32 near proximal end 16. Probe housing 11 may be formed from polyurethane, ABS plastic, or the like.

Transducer region 30 of probe housing 11 is cylindrical in shape to facilitate transrectal insertion. Transducer member 28 is disposed within an interior volume defined by transducer region 30, but does not contact probe housing 11 in the transducer region, being cantilevered from the handle region 32 instead. Transducer member 28 is thus free to both rotate about the axis of transducer region 30 and to translate axially. Window 20 provides passage for ultrasonic energy within a range of axial and angular positions of the active surfaces of transducer 28, as seen in FIG. 3 Disposed about distal end 18 of transducer region 30 is an acoustical membrane 38.

Contained within handle region 32 of housing 11 are a transducer positioning means 34 and a fluid reservoir 36. Positioning means 34 will provide linear and sector scanning motion to transducer member 28 relative to housing 11, as well as providing position feedback to controller 12. An exemplary positioning means was described in parent application Ser. No. 08/840,502. A pair of sliding seals 42 prevent fluid from entering around transducer member 28. Fluid reservoir 36 contains coupling fluid and is in fluid communication with transducer region 30 through a fluid pressurization and recirculation system. Finally, handle region 32 will include means for securing the probe in a fixed position relative to a patient body, typically utilizing a releasably fixed support attached to a table (not shown).

The Transducer Member

Referring now to FIGS. 5–8, the transducer member of the present invention will include a plurality of active surfaces having differing focal geometries. By selectively orienting and radiating from one of the active surfaces, tissues at differing distances can be treated. Each therapeutic active surface is preferably of the type disclosed in U.S. Pat. No. 5,117,832, previously incorporated by reference.

Figure 5:
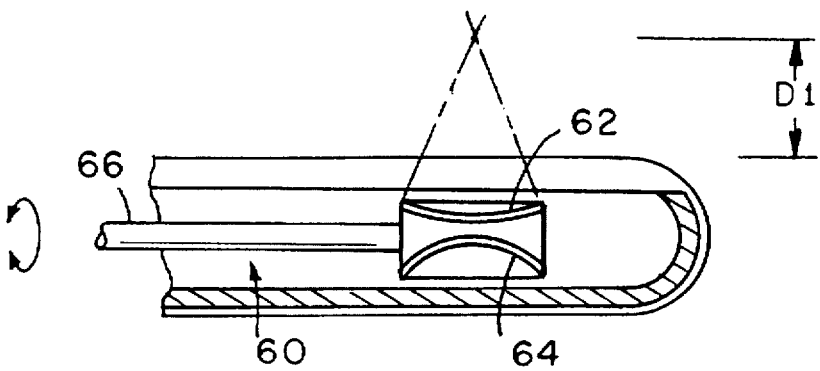

As seen in FIG. 5, a back-to-back transducer member 60 includes a first active surface 62 and a second active surface 64. The transducer surfaces are radially opposed, and are supported by transducer shaft 66. The active surfaces each have a fixed focal geometry which focuses radiated ultrasonic energy. First active surface 62 focuses energy at a distance D1 from the transducer member.

Figure 6:
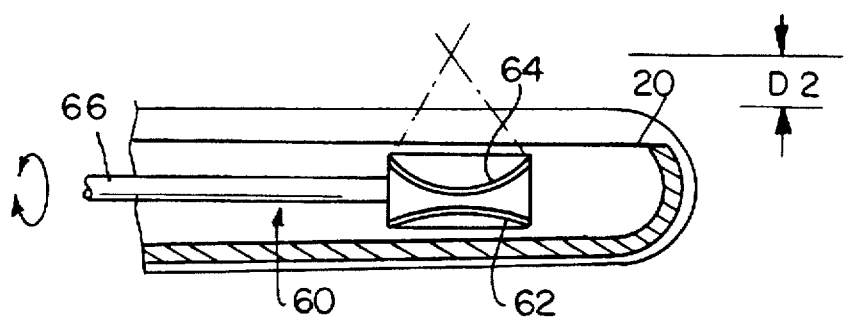
FIGS. 5 and 6 are cross-sectional views of an embodiment of the present multifaceted transducer member having back-to-back active surfaces, shown within the probe housing of the present invention.

As seen in FIG. 6, back-to-back transducer member 60 may be rotated about shaft 66 by 180° to orient the second active surface 64 through acoustic window 20. When second active surface 64 is energized, it focuses active energy at a second distance D2 which is less than first distance D1.

The present ultrasound therapy system is able to select between two different active surfaces by rotating transducer 60 by 180°. It has been found that two active surfaces are sufficient to apply therapy for focal diseases of the prostate such as BPH where the total therapy volume ranges from at least 2 cm to 5 cm. For such therapy ranges, the first active surface will generally focus at a volume in the range from 2 cm to 4 cm. The second volume will overlap the first by 0% to 50%. Individual treatment volume will preferably be in the range from 1 mm to 4 mm at the widest point when discrete volumes are treated. Treatment lesions will typically taper both towards and away from the probe, the widest point being roughly in the middle. The amount of taper will determine the amount of overlap.

Treatment range and control are preferably increased by separating each active surface into at least inner and outer regions with phase control between them, as described herein below. Clearly, the cost and complexity will rise with the number of active surfaces and regions.

Ultrasound energy is selectively radiated from the active surfaces of the present invention by selectively supplying wires connected to the first or second active surface with high frequency alternating electrical current, as will be well understood in the art. A particularly advantageous power supply system is an electronic switch, such as a field effect transistor having a filter for transients and harmonics. Radiated noise is reduced by switching at the zero cross over point. Such a system provides a considerably lighter and less costly power supply, as compared to other commercially available units, for generating the required frequencies of the 4 Mhz range.

Figure 7:
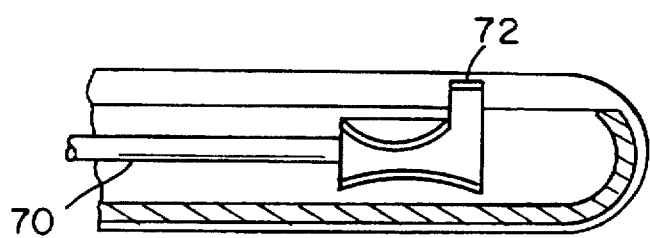
FIG. 7 is a cross-sectional view of a preferred embodiment of a multi-faceted transducer member having a separate imaging surface, shown within the probe housing of the present invention.

FIG. 7 illustrates a preferred embodiment of the present transducer member having two active therapeutic surfaces back-to-back, and also having a third active surface which radiates and receives imaging ultrasound energy. A three-in-one transducer member 70 includes two active surfaces analogous to first and second active surfaces 62 and 64 described above. Additionally, a third transducer surface 72 having a focal geometry which is optimized for transmission and receiving of imaging ultrasound. While a wide variety of imaging transducers are known in the art which might be used, transducer surface 72 preferably has a spherical concave shape. Alternatively, an array transducer will provide added capabilities, but at a higher cost. Advantageously, 3 in 1 transducer member 70 allows placement of the imaging transducer in close proximity to the acoustic coupling membrane 38, which will reduce reflections and reverberations from that surface and improve image quality. Specifically, the cylindrical geometry of the membrane maintains a constant small gap between the imaging transducer and the membrane wall as the transducer scans in cylindrical coordinates.

The selection of an array imaging transducer for transducer surface 72 will add significantly to the imaging capabilities of the present probe. Arrays provide independent electronic scanning which can be combined with a mechanical scan to produce a 3-D image in a single pass. Arrays further provide color doppler imaging of blood flow or flow through a fallopian tube. The monitoring of tissue movements is also useful in elasticity imaging, as discussed hereinbelow. The array may be either arranged along the axial length of transducer surface 72, or may be arranged across the width of the transducer surface 72. Optionally, the imaging transducer may be disposed on the edge of a transducer member between the therapeutic active surfaces, or opposite a single therapeutic active surface.

Figure 8:
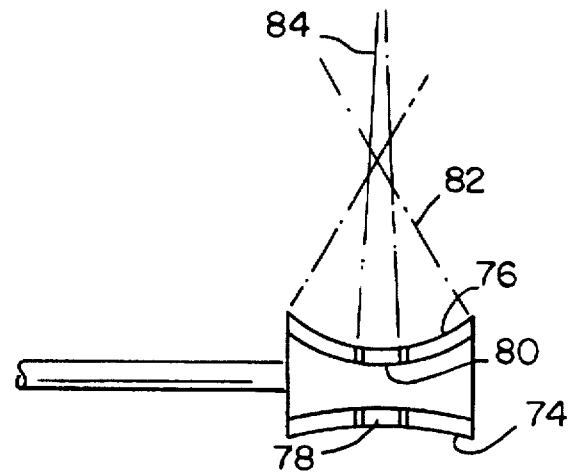
FIG. 8 is a cross-sectional view of another embodiment of a back-to-back transducer member having imaging regions on each active surface.

FIG. 8 illustrates an alternative embodiment of the present multifaceted transducer member having first and second active surfaces 74, 76 with imaging regions 78, 80. The imaging regions provide focused therapeutic energy 82 together with the remainder of the active surface, but are also able to separately radiate and receive imaging ultrasound energy 84. The focal geometry of the combined active surface may be modified, for example, having a greater focal length, to improve image quality. Advantageously, phase adjustments of the power supplied to the central imaging region relative to the surrounding active surface also provides a limited amount of modification to the effective focal geometry, allowing electronic manipulation of the lesion length and location. Thus, imaging regions 78 and 80, and active surfaces 74 and 76, are alternatively used as simple phased arrays to vary focal depth, even where a dedicated imaging transducer is included, as shown in FIG. 10. Such phase control allows variation in focal character of over 0.25 cm, preferably being about 0.5 cm. Clearly, separate power supply wires must be provided for the inner and outer regions. Additional intermediate regions will increase targeting precision, but will also increase cost and complexity.

In addition to providing a wider therapy range, multiple active surfaces of the present transducer member promote treatment with greater precision and therapy of smaller and more localized targets. As an example, HIFU therapy applied along vessels and tubes which are radially oriented from the probe will be greatly improved. Therefore, one particular advantageous use of the present multi-focus probe is cautery along the horn and interstitial area of the fallopian tubes to effect sterilization.

The Membrane

Referring again to FIG. 4, disposed about the distal portion of transducer region 30 so as to cover acoustic window 20 is acoustic coupling membrane 38. In this embodiment, acoustic membrane 38 is formed as a cylinder which is sealed at the distal end, and is sealingly attached to probe housing 11 at fitting 40. Transducer region 30 and acoustic membrane 38 thereby define an enclosed volume which is open only to handle region 32 through the fluid pressurization and recirculation system.

Acoustic membrane 38 must fulfill three conflicting HIFU probe design requirements. First, the membrane must provide transmission of ultrasound energy to adjacent tissue. The membrane should not absorb the energy as heat, or therapeutic effectiveness will be reduced and thermal injury to the adjacent tissue will result. Prior art ultrasound membranes have generally used absorptive elastic polymers which rely on thickness to provide strength and maintain their shape. The thickness of such membranes results in significant absorption. In connection with the present invention, it has been found that efficient transmission of energy is provided by a thin, flexible, inelastic non-distensible membrane.

The second design requirement for a HIFU probe membrane is to separate the transducer member from the adjacent tissue. Without such separation, tissue in direct contact with a scanning transducer member may be injured, or may cause damage to the transducer or the scanning movement means (See FIG. 2). Thus, the acoustic membrane should separate the transducer member and tissue while the membrane is pressed against the adjacent tissue to ensure proper coupling. Moreover, it would be advantageous to allow compression of the tissue by the membrane to position the housing relative to the target tissue. This separation of the tissue from the transducer member is especially important in the present HIFU system, which relies on rotating or flipping of the back-to-back transducer member within a cylindrical housing, which could otherwise pinch tissue and bind the movement means. Such separation would be aided by a rigid membrane.

The third and final HIFU probe membrane design requirement is to provide undistorted propagation of the ultrasound energy. Distortion of the ultrasound wave energy may result in either unfocusing of the wave path from the target tissue, or alternatively, in reflecting energy back into the transducer housing. Clearly, ultrasonic wave propagation from the therapeutic radiating active surfaces is ideally unaffected by the orientation of the transducer member within the range of window 20. It has been found that a thin acoustic membrane minimizes both distortion and critical angle phenomenon reflections of ultrasonic waves.

Referring now to FIG. 9, a schematic axial view of back-to-back transducer member 28 helps explain critical angle phenomenon losses. Active surface 50 radiates focused ultrasound energy 52 through membrane 54 and into tissue 58. First assuming that membrane 54 is relatively thick, T being over 1 wavelength, if the angle of incidence θ between the outermost edge of focused energy 52 is larger than a critical angle, the outermost portion of the energy will be reflected by the inner surface of the membrane rather than passing through to the adjacent tissue. This loss is particularly problematic for the relatively large active surfaces associated with HIFU, which generally feature a large encompassed angle.

The critical angle varies as a function of the relative speed of wave propagation through membrane 54 and a coupling fluid 56 surrounding the transducer member, the reflections increasing as the difference in relative propagation speeds increases. Unfortunately, there tends to be a considerable difference in propagation speed for suitable membrane materials as compared to suitable coupling fluids. It will further be recognized that another similar reflection may occur at the outer surface of the membrane.

If membrane 54 is instead assumed to be relatively thin, focused ultrasound energy 52 is transmitted with much greater efficiency. The effective perturbation in wave propagation through the membrane diminishes as thickness decreases. With thin membranes, T being less than 1 wavelength and preferably being less than 0.1 wavelengths, the membrane becomes transparent to sound, and the critical angle phenomenon will be determined by the difference in propagation speeds between the coupling fluid and the tissue 58. As it is much easier to match the speed of propagation through the coupling fluid to the speed of propagation through the tissue, critical angle losses can be decreased dramatically. Optionally, the membrane thickness may be tailored to the frequency, preferably being ¼ wavelength for membranes with high ultrasound velocities, or ½ membranes with low ultrasound velocities.

Finally, it will be understood that any distortion caused by membrane 54 on focused ultrasound wave 52 will not vary with the position of the transducer member, where membrane 54 is formed as a cylinder with an axis coinciding with the axis of rotation and translation of transducer member 28. Thus a focusing transducer which will transmit through such a cylindrical membrane can easily have its focal geometry tailored to provide an accurate focal point.

Referring now to FIG. 10, acoustic membrane 38 is formed from a thin, flexible material to provide efficient transmission of ultrasound energy with minimal critical angle losses. Additionally, the material of membrane 38 is an inelastic and non-distensible material which is "rigidized" by stress. An inelastic membrane held under sufficient tension will not deflect significantly when a force F is imposed against the membrane surface. Suitable materials for acoustic membrane 38 include PET, poly amide, and polyethylene.

The preferred acoustic membrane is formed as a cylinder with one end closed but without any seams. The membrane may be formed by methods developed for forming inelastic balloons used in balloon angioplasty. The closed end is formed by melting the plastic at the end of a cylindrical membrane. Advantageously, the membrane will allow inspection for air bubbles trapped in the membrane/tissue interface, preferably using optical fibers methods.

As described in detail hereinbelow, tension is applied to acoustic membrane 38 by a coupling fluid pressurization and recirculation system. Fluid pressure P acts against the interior surface of the cylindrical membrane, loading the membrane in tension and helping to counteract inward force F. Therefore, acoustic coupling membrane 38 provides a rigidized surface which can withstand pressure from adjoining tissues, including during direct manipulation, while effectively separating tissue from transducer member 38 within transducer region 30.

Referring now to FIGS. 11 and 12, an alternative, though not necessarily preferred, embodiment of the acoustic membrane will be described. In FIG. 11 an elastic membrane 8, typically a condom, is disposed over the distal end of the probe housing. Pressurized coupling fluid is again supplied through the probe housing, but as the membrane is elastic, it expands outward. To ensure that protruding tissue does not deform the membrane locally so as to interfere with the movement of transducer member 60, a spring clip 90 restrains the expansion of membrane 8 over most of the probe housing, with the exception of the area of a window 92. Thus, the pressure of the coupling fluid acts to expand membrane 8 primarily at window 92, to displace any tissue where protruding tissues would otherwise pose a risk.

The attachment of spring clip 90 is best seen in FIG. 12. The spring clip is made of a metal or some other resilient material, and expands to lock over membrane 8 and onto the probe housing.

FIG. 11 further illustrates an alternative embodiment of the present probe housing having an enclosed area in which the transducer member may be safely flipped. Probe housing 94 includes a proximal "park area" 96 which is proximal of window 92. Transducer member 60 is axially movable to be radially enclosed within park area 96. Once in that position, transducer member 60 can be rotated 180° with little danger of injuring tissue protruding into window 92. Thus the park area allows safe flipping to select an active surface. Clearly, a similar distal park area could instead be used.

FIG. 13 is a still further embodiment of the present acoustic coupling membrane which utilizes a thin, flexible, inelastic membrane which is rigidized by applying a tensile load. A membrane 100 is again formed as a cylinder having a closed distal end. Probe housing 102 extends distally within the membrane, and includes housing threads 104 which mate with membrane threads 106. By rotating the membrane threads relative to the housing threads, distal end of housing 102 is compressed by membrane 100. The inelastic membrane cylinder is placed under a tensile load, which rigidizes the membrane.

Figure 14:
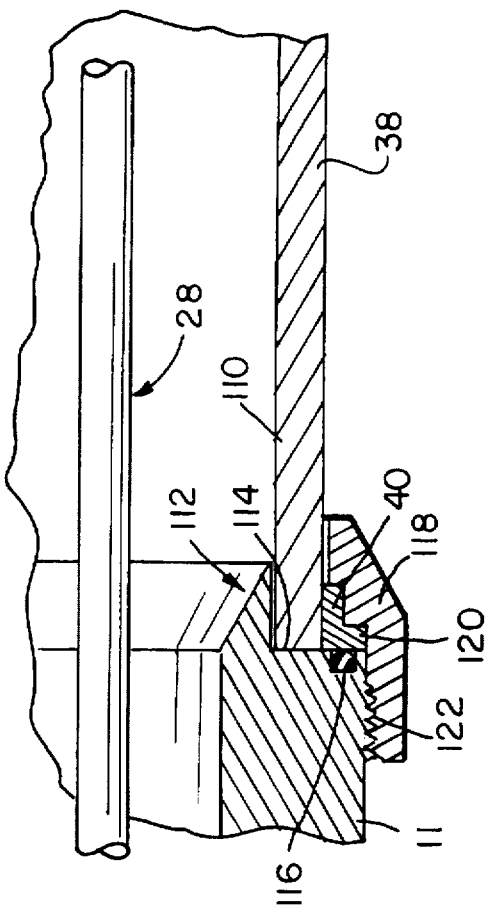
FIG. 14 is a cross-sectional view of a preferred method of attaching the cylindrical, thin, flexible, inelastic membrane to a probe housing of FIG. 4.

Finally, FIG. 14 is a detailed view of a preferred embodiment of fitting 40, as seen in FIG. 4. Transducer member 28 is disposed within distal region 30 of probe housing 11, only one side of which is shown. In this embodiment, probe housing 11 has a distal tip 110 joined to the rest of probe housing 11 at joint 112. Tip 110 rests against an annular shelf 114, which has a slot 116 outside of tip 110. Slot 116 holds an O-ring or some other sealing means.

Attached to the proximal end of acoustic membrane 38 is an annular collar 118. Collar 118 is bonded and sealed to the acoustic membrane. Collar 118 and acoustic membrane 38 fit over tip 110 and rests against shelf 114 over slot 116. Fitting 40 then fits over the membrane and collar, until a rim 120 of fitting 40 engages a lip on collar 118. Fitting 40 further has threads 122 which mate with threads on housing 11, which clamp collar 118 onto ledge 114 over slot 116. The sealing means within the slot are thereby compressed, sealing acoustic membrane 38 to probe housing 11.

Clearly, other methods for sealingly attaching the acoustic membrane to the probe housing are also available. One alternative embodiment replaces fitting 40 with a large lure fitting. It is preferably, however, to include means for easily replacing the membrane, particularly where the membrane is formed as a cylinder which is closed at the distal end. The membrane thereby keeps the remainder of the probe sterile, and can be sterilized while attached to the probe to avoid the time-consuming process of filling the interior volume with coupling fluid after each use. Moreover, the membrane is easily replaced when it degrades or becomes worn.

Pressurization System

Referring once again to FIG. 4, probe 10 includes a pressurization system which rigidizes the acoustic membrane and recirculates pressurization fluid, thereby provide cooling of the distal region 30 of probe housing 11, specifically cooling transducer member 28 and acoustic membrane 38.

As described above, handle region 32 of probe housing 11 includes coupling fluid reservoir 36. Reservoir 36 is in fluid communication with distal region 30 through two passages: a supply lumen 126 and a return lumen 128. Two check valves 130, one on each lumen, ensure that the fluid is recirculated by preventing fluid from returning through supply lumen 126 or being supplied through return lumen 128. An extension 132 on the distal end of supply lumen 126 directs cool fluid toward distal end 18 of housing 11, while return lumen 128 removes more proximal fluid, thus cooling the entire interior volume of distal region 30.

The pressurization system compensates for linear motion of the transducer member so that the pressure remains largely constant. Transducer member 28 extends from distal region 30 into fluid reservoir 36. The cross section of the shaft of transducer member 28 is constant, which results in the same volume entering reservoir 36 as is leaving the distal region 30 when transducer member 28 moves proximally past sliding seals 42. Fluid flows from the reservoir to distal region 30 through supply lumen 126 to compensate. Similarly, fluid flows from distal region 30 back to reservoir 36 to compensate when transducer member 28 moves distally. However, the total of the two volumes remains constant, allowing the reservoir to be pressurized and sealed. Moreover, by oscillating the transducer back and forth with a linear motion, as required for a linear scan, fluid is pumped through the recirculating system.

The recirculating system described above also provides the pressure to rigidize acoustic membrane 38. A pressurizing piston 134 is connected to handle region 32 by proximal threads 136. As the piston tightens on reservoir 36, pressure is transmitted through supply lumen 126 to distal region 30. Thus the pressure against the membrane can be varied from the proximal housing, even while the transducer is in use.

Figure 15:
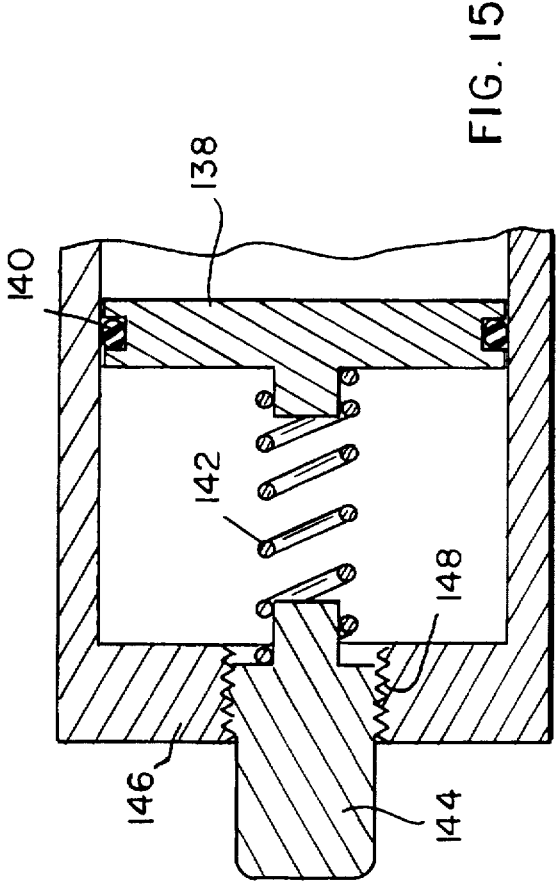
FIG. 15 is a preferred pressurization control mechanism for the pressurization reservoir of the probe of FIG. 4.

A preferred embodiment of the pressurization piston is shown in FIG. 15. A piston 138 having an O-ring 140 is attached to a spring 142. Spring 142 is compressed by a knob 144 attached to a proximal wall 146 by threads 148. Rotation of knob 144 thus varies the compression of spring 142, but the spring may be designed to limit the maximum compression, avoiding bursting of acoustic membrane 38 (see FIG. 4). The pressurization system preferably provides a coupling fluid pressure in the range from 1 psi to 5 psi.

As described above, the ultrasonic energy throughput with an internal therapeutic probe is limited by heat buildup. The recirculating pressurization system of the present probe therefore increases throughput by removing excess heat. Additional measures may be required, including continuous pumping of fluid or active cooling of the fluid in the reservoir. Active cooling is preferably supplied by reverse thermocouples at the reservoir, requiring little added complexity. Alternatively, A continuous supply of cool coupling fluid, such as water, could be used.

Increased throughput may alternatively be obtained by increasing the transmission efficiency of the transducer member, the acoustic membrane, or the coupling fluid. As described above, transmission efficiency may be improved by preventing the formation of bubbles through the use of degassed coupling fluid. Additionally, the present recirculation system may incorporate a bubble trap (not shown) in either supply lumen 126 or return lumen 128. Thus any bubbles which do form will be eliminated during recirculation, improving efficiency and resolution. Additionally, such bubble traps will facilitate elimination of any bubbles which are introduced to the probe when the acoustic membrane is replaced.

The present pressurization system may further be incorporated into an elasticity imaging system. As described in U.S. Pat. No. 5,178,147, the full disclosure of which is incorporated herein by reference, detection of thermal lesions is facilitated by monitoring a gross tissue displacement. Lesion detection is possible due to the increased tissue stiffness of the lesion relative to untreated tissue. Conveniently, rapid variations in pressure provided by the pressurization system will initiate the required tissue displacement, particularly when the membrane pulsates with the coupling fluid.

Controller and Operation

Figure 16:
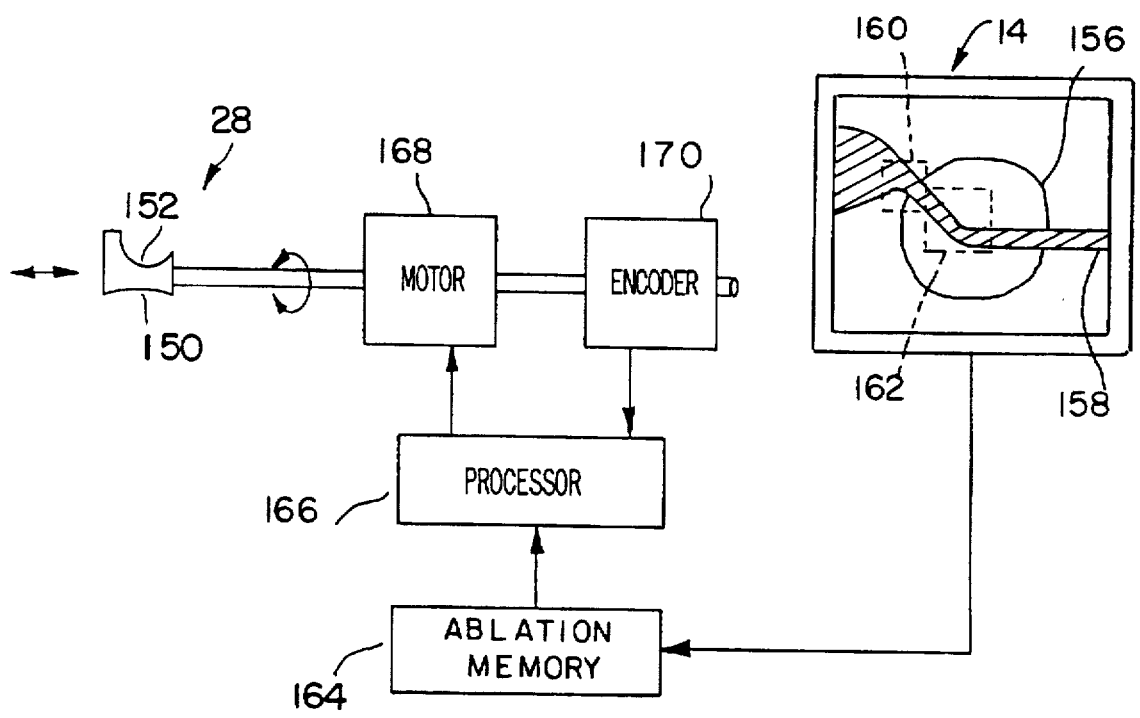
FIG. 16 is simplified schematic of the present control means.

Referring now to FIG. 16, the HIFU system of the present invention further provides a controller capable of taking advantage of the increased capabilities of the present intracavity probe. The HIFU system controller will generally include display means, input means such as a keyboard and a trackball, a general purpose computer processor (including memory and storage devices), a digitizer capable of digitizing analogue signals and interfacing with the processor for ultrasonic data input and display, and an RF generator and amplifier for selectively powering the active surfaces of the transducer member. The selection and arrangement of such controller elements are described in detail in parent application Ser. No. 07/840,502, previously incorporated by reference.

The present control and positioning system, schematically illustrated in FIG. 16, broadly comprises a controller coupled to a transducer member positioning means. The controller includes a display means 14, an ablation memory 164, and a processor 166. Positioning means 34 (shown in FIG. 4) is located in the probe handle, and includes a rotational positioning motor 168 and a rotational position indicating encoder 170. Advantageously, this control and positioning system allows use of a single motor located in the handle of the probe for angular aiming of a transducer member 28, sector scanning during imaging, and selection between back-to-back active surfaces 150 and 152 by rotating transducer member 28 to orient the selected active surface through the window 20 of probe housing 11 (see FIG. 3).

As described above, the operator of a HIFU system according to the present invention will visually select a target treatment volume using display means 14. To provide an image of the tissue including the target tissue, the tissue is ultrasonically imaged using transducer member 28 and displayed on display means 14. The display shown is representative of a linear scan in which tissues which are closer to the probe housing appear at the bottom of the screen, while more distant tissues appear at the top of the screen.

The operator selects a treatment volume, for example, by manipulation of a trackball, a mouse, or the like. As shown, a diseased prostate 156 surrounding a urethra 158 has had a treatment volume selected which is composed of two adjacent target regions. A first target region 160 is at a first distance from the probe housing, a second target region 162 is at a second distance closer to the probe housing. As described above, the actual target ranges associated with the first and second target distances can be seen to overlap, ensuring that the probe can apply therapy to tissues throughout a continuous range. The selected treatment volume is stored in an ablation memory 164.

The application of therapeutic energy will be aimed and directed by a processor 166. Processor 166 reads ablation memory 164, using the information to direct motor 168 to rotate transducer member 28. The angular position of transducer 28 is fed back to processor 166 by encoder 170. Similarly, the processor will also control the linear position of the transducer member using a linear motor and linear encoder (not shown). The processor 166 then energizes first surface 150, which focuses ablating energy on tissue within first region 160.

The processor continues to redirect and ablate tissue until the first region is fully ablated, optionally imaging the tissue intermittently to confirm that the relative position of the probe and the target have not changed. The processor then directs the motor to rotate transducer member 28 by 180°, and repeats the process with the second target region, using second active surface 152, which has a shorter focal distance than the first active surface. In certain cases, in order to allow blood perfusion cooling of areas of the prostate requiring protection from heat, the firing sequence may be changed so that first region 160 and second region 162 are treated alternately or in a selected order dictated by thermal concerns.

Figure 17:
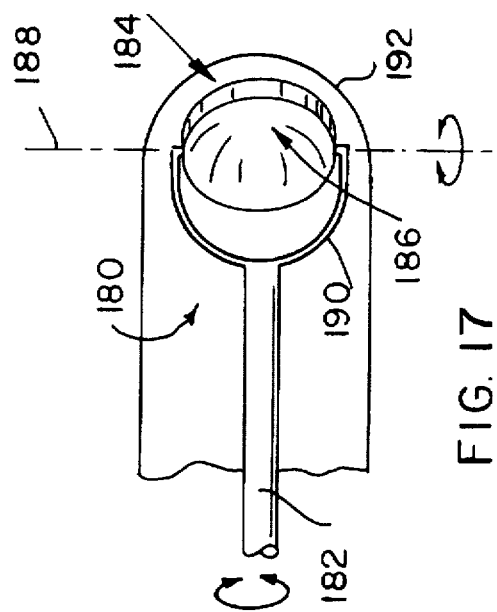
FIG. 17 is an alternative embodiment of the present probe having back-to-back active surfaces which move in spherical coordinates behind a forward looking acoustic window.

Although the specific embodiments have been described in detail, various alternatives, modifications, and equivalents may be used. For example, FIG. 17 illustrates an alternative embodiment of the present transducer member which provides "forward facing" therapy. Transducer member 180 rotates about shaft 182 as described above. However, first and second active surfaces 184, 1L86 also rotate about axis 188 supported by yoke 190. Thus, the active surfaces are manipulated in spherical coordinates, and may again apply ultrasound therapy at two distances by flipping between active surfaces 184, 186. Use of this embodiment through a spherical acoustic membrane 192 will avoid distortion, similar to the use of the cylindrical membrane with cylindrical coordinates described above. Furthermore, therapeutic energy may be applied "forward" or distally of acoustic membrane 192.

Additional alternatives may also be used. Therefore, the above description should not be taken as limiting the scope of the invention, which is instead defined by the appended claims.

What is claimed is:

1. An ultrasound probe comprising a housing having an interior, a first ultrasound radiating surface, a selectively movable support for supporting the first radiating surface, the support having a first end on which the first radiating surface is mounted, and a second end opposite the first end, a seal through which the support extends, the seal dividing the interior into a first chamber at a first end thereof in which the first radiating surface is housed and a second chamber at a second end thereof into which the second end extends, at least a first passageway coupling the first and second chambers, and a piston for closing the second chamber, the piston being movable selectively to alter the volume of the second chamber, and a fluid medium for filling the probe, the fluid medium serving to couple ultrasound between the first radiating surface and a tissue being investigated with the aid of ultrasound transmitted from the first radiating surface, movement of the support to reciprocate the first radiating surface reciprocating the second end of the support in the second chamber to pump the fluid medium back and forth between the first and second chambers, and movement of the piston selectively to reduce and increase the volume of the second chamber increasing and decreasing, respectively, the pressure of the fluid medium in the first and second chambers.

2. The probe of claim 1 wherein the first chamber comprises an acoustically substantially transparent window for coupling ultrasound between the first radiating surface and the tissue being investigated, the acoustically substantially transparent window including an elastically deformable portion separating the first chamber from the exterior of the probe, movement of the piston to decrease the volume of the second chamber elastically deforming the elastically deformable portion.

3. The probe of claim 2 further comprising a second radiating surface mounted on the first end of the support, the support being selectively rotatable to orient the second radiating surface to radiate ultrasound through the acoustically substantially transparent window.

4. The probe of claim 3 and further comprising a second passageway for coupling the first and second chambers, a first one-way valve in the first passageway to prevent fluid flow from the first chamber into the second, and a second one-way valve in the second passageway to prevent fluid flow from the second chamber into the first.

5. The probe of claim 2 and further comprising a second passageway for coupling the first and second chambers, a first one-way valve in the first passageway to prevent fluid flow from the first chamber into the second, and a second one-way valve in the second passageway to prevent fluid flow from the second chamber into the first.

6. The probe of claim 5 wherein the first passageway terminates at a first location within the first chamber and a second location in the second chamber, and the second passageway terminates at a third location in the first chamber and a fourth location in the second chamber, the first location being remote from the third location and the second location being remote from the fourth location.

7. The probe of claim 1 and further comprising a second passageway for coupling the first and second chambers, a first one-way valve in the first passageway to prevent fluid flow from the first chamber into the second, and a second one-way valve in the second passageway to prevent fluid flow from the second chamber into the first.

8. The probe of claim 7 wherein the first passageway terminates at a first location within the first chamber and a second location in the second chamber, and the second passageway terminates at a third location in the first chamber and a fourth location in the second chamber, the first location being remote from the third location and the second location being remote from the fourth location.

9. The probe of claim 4, 5 or 7 wherein the first passageway terminates at a first location within the first chamber and a second location in the second chamber, and the second passageway terminates at a third location in the first chamber and a fourth location in the second chamber, the first location being remote from the third location and the second location being remote from the fourth location.

* * * * *